(12) United States Patent
Milton-Edwards et al.

(10) Patent No.: US 10,058,661 B2
(45) Date of Patent: Aug. 28, 2018

(54) INHALATION MONITORING SYSTEM AND METHOD

(71) Applicant: Norton (Waterford) Limited, Waterford (IE)

(72) Inventors: Mark Milton-Edwards, Macclesfield (GB); Henry Chrystyn, Bingley (GB); Mark Steven Morrison, Basking Ridge, NJ (US); Douglas E. Weitzel, Hamilton, NJ (US)

(73) Assignee: Norton (Waterford) Limited, Waterford (IE)

( * ) Notice: Subject to any disclaimer, the term of this patent is extended or adjusted under 35 U.S.C. 154(b) by 363 days.

(21) Appl. No.: 14/802,675

(22) Filed: Jul. 17, 2015

(65) Prior Publication Data

US 2016/0158469 A1    Jun. 9, 2016

Related U.S. Application Data

(60) Provisional application No. 62/087,567, filed on Dec. 4, 2014, provisional application No. 62/087,571, filed on Dec. 4, 2014.

(51) Int. Cl.
*A61B 5/08* (2006.01)
*A61B 5/091* (2006.01)
(Continued)

(52) U.S. Cl.
CPC ....... *A61M 15/0025* (2014.02); *A61B 5/0871* (2013.01); *A61B 5/091* (2013.01); *A61B 5/4839* (2013.01); *A61B 5/7275* (2013.01); *A61M 15/00* (2013.01); *A61M 16/0003* (2014.02); *A61M 16/0051* (2013.01); *A61M 16/021* (2017.08);
(Continued)

(58) Field of Classification Search
CPC .......... A61M 15/0025; A61M 16/0003; A61M 15/00; A61M 16/0051; A61M 15/0026; A61M 15/0051; A61M 15/0081; A61M 11/02; A61M 2016/0027;
(Continued)

(56) References Cited

U.S. PATENT DOCUMENTS

| 5,392,768 A | * | 2/1995 | Johansson | A61M 15/00 |
| | | | | 128/200.14 |
| 5,394,866 A | * | 3/1995 | Ritson | A61M 15/00 |
| | | | | 128/200.14 |

(Continued)

FOREIGN PATENT DOCUMENTS

| JP | 2007-525236 A | 9/2007 |
| RU | 2382657 C1 | 2/2010 |

(Continued)

*Primary Examiner* — Navin Natnithithadha
(74) *Attorney, Agent, or Firm* — Condo Roccia Koptiw LLP

(57) ABSTRACT

An inhalation monitoring system includes an inhaler having a medicament delivery apparatus configured to deliver medicament to a user during an inhalation of the user; inhalation monitoring apparatus, configured to, during the inhalation, gather data for determining a measure of the user's lung function and/or lung health; and a processor configured to receive the data from the inhalation monitoring apparatus and, using the data, determine a measure of the user's lung function and/or lung health.

24 Claims, 3 Drawing Sheets

(51) Int. Cl.
*A61M 15/00* (2006.01)
*A61M 16/00* (2006.01)
*A61M 11/02* (2006.01)
*A61B 5/087* (2006.01)
*A61B 5/00* (2006.01)
*G06F 19/00* (2018.01)

(52) U.S. Cl.
CPC .............. *G06F 19/00* (2013.01); *A61M 11/02* (2013.01); *A61M 15/0026* (2014.02); *A61M 15/0051* (2014.02); *A61M 15/0081* (2014.02); *A61M 2016/0027* (2013.01); *A61M 2202/064* (2013.01); *A61M 2205/18* (2013.01); *A61M 2205/3331* (2013.01); *A61M 2205/3553* (2013.01); *A61M 2205/3592* (2013.01); *A61M 2205/50* (2013.01); *A61M 2205/502* (2013.01); *A61M 2205/8206* (2013.01); *A61M 2209/06* (2013.01); *A61M 2230/40* (2013.01)

(58) Field of Classification Search
CPC ........... A61M 2202/064; A61B 5/0871; A61B 5/091; A61B 5/4839; A61B 5/7275
USPC .................................................. 600/529–543
See application file for complete search history.

(56) References Cited

U.S. PATENT DOCUMENTS

| | | | | |
|---|---|---|---|---|
| 5,404,871 A | * | 4/1995 | Goodman | A61M 15/00 128/200.14 |
| 5,450,336 A | * | 9/1995 | Rubsamen | A61M 15/0091 341/120 |
| 5,456,264 A | | 10/1995 | Series et al. | |
| 5,469,750 A | * | 11/1995 | Lloyd | A61M 15/00 73/1.34 |
| 5,497,764 A | * | 3/1996 | Ritson | A61M 15/00 128/200.14 |
| 5,520,166 A | * | 5/1996 | Ritson | A61M 15/00 128/200.14 |
| 5,522,378 A | * | 6/1996 | Ritson | A61M 15/00 128/200.14 |
| 5,608,647 A | * | 3/1997 | Rubsamen | A61M 15/0091 128/204.18 |
| 5,622,162 A | * | 4/1997 | Johansson | A61M 15/00 128/200.14 |
| 5,743,252 A | * | 4/1998 | Rubsamen | A61M 15/0091 128/200.14 |
| 5,755,218 A | * | 5/1998 | Johansson | A61M 15/00 128/200.14 |
| 8,834,848 B2 | * | 9/2014 | Muellinger | A61M 11/06 128/200.16 |
| 8,910,625 B2 | * | 12/2014 | Mullinger | A61M 11/005 128/200.14 |
| 2005/0119586 A1 | | 6/2005 | Coyle et al. | |
| 2006/0185672 A1 | | 8/2006 | Pinon et al. | |
| 2009/0020113 A1 | | 1/2009 | Watanabe et al. | |
| 2009/0156952 A1 | | 6/2009 | Hunter et al. | |
| 2013/0037024 A1 | * | 2/2013 | Muellinger | A61M 11/06 128/203.12 |
| 2014/0116426 A1 | * | 5/2014 | Mullinger | A61M 11/005 128/200.14 |
| 2014/0158126 A1 | | 6/2014 | Parry-Billings et al. | |
| 2014/0202457 A1 | | 7/2014 | Addington et al. | |
| 2015/0165137 A1 | * | 6/2015 | Mullinger | A61M 11/005 128/200.16 |

FOREIGN PATENT DOCUMENTS

| | | |
|---|---|---|
| WO | WO 2005/046426 A2 | 5/2005 |
| WO | WO 2008/149959 A1 | 12/2008 |
| WO | WO 2011-135353 A1 | 11/2011 |
| WO | WO 2013/098714 A1 | 7/2013 |

* cited by examiner

INHALATION MONITORING SYSTEM AND METHOD

CROSS-REFERENCE TO RELATED APPLICATIONS

This non-provisional patent application claims priority to U.S. Provisional Patent Application No. 62/087,567, filed Dec. 4, 2014, and U.S. Provisional Patent Application No. 62/087,571, filed Dec. 4, 2014, each of which is incorporated by reference herein in its entirety and for all purposes.

FIELD OF THE INVENTION

This invention is related to an inhaler, an inhalation monitoring system and a method for monitoring an inhaler.

BACKGROUND OF THE INVENTION

Inhalers or puffers are used for delivering medication into the body via the lungs. They can be used, for example, in the treatment of asthma and chronic obstructive pulmonary disease (COPD). Types of inhalers include metered dose inhalers (MDIs), Soft Mist Inhalers (SMIs), nebulisers and dry powder inhalers (DPIs).

A tidal inhaler is a class of inhaler in which the medication is consumed in multiple successive inhalations (referred to as tidal breaths) rather than a single inhalation. The patient uses their normal at rest breathing pattern without an exaggerated inhalation flow rate, also known as forced inhalation maneuver.

A spirometer is an apparatus for measuring the volume of air inspired and expired by a patient's lungs. Spirometers measure ventilation, the movement of air into and out of the lungs. From the traces, known as spirograms, output by spirometers, it is possible to identify abnormal (obstructive or restrictive) ventilation patterns. Existing spirometers use a variety of different measurement methods including pressure transducers, ultrasonic and water gauge.

Peak flow meters are used to measure peak expiratory flow (PEF), also called peak expiratory flow rate (PEFR). This is a person's maximum speed of expiration. PEF correlates with the airflow through the bronchi and thus the degree of obstruction in the airways. Peak flow readings are lower when the airways are constricted, for example due to an exacerbation of a lung condition. From changes in recorded values, patients and doctors may determine lung functionality, severity of symptoms, and treatment. Peak flow meters can also be used for diagnosis.

Spirometers and peak flow meters are generally used to monitor the lung function and/or lung health of individuals, in particular lung patients suffering from conditions such as asthma and COPD. Lung function is defined according to expiratory measures, such as PEF.

Another measure of lung function is forced expiratory volume in 1 second ($FEV_1$). $FEV_1$ is the volume of air that can forcibly be blown out in one second, after full inspiration. In obstructive diseases (e.g. asthma, COPD, chronic bronchitis, emphysema) $FEV_1$ is diminished because of increased airway resistance to expiratory flow.

Patient lung function is generally monitored during appointments with medical practitioners, periodically or in response to a recurrence or worsening of symptoms. For reasons of practicality, monitoring is typically quite infrequent during periods of apparent good health. Reactive treatment is therefore not always administered as soon as it ideally would be, and preventative treatment can be used more than necessary.

Some patients find spirometers and peak flow meters tricky to use and may need training and supervision in their use. Due to this, and for reasons of cost, most patients do not possess personal spirometers or peak flow meters.

What is needed is an improved means of monitoring lung function and/or health for patients with obstructive lung conditions.

SUMMARY OF THE INVENTION

According to a first aspect, there is provided an inhalation monitoring system comprising: an inhaler comprising medicament delivery apparatus configured to deliver medicament to a user during an inhalation of the user; inhalation monitoring apparatus, configured to, during said inhalation, gather data for determining a measure of the user's lung function and/or lung health; and a processor configured to receive said data from said inhalation monitoring apparatus and, using the data, determine a measure of the user's lung function and/or lung health.

The inhaler could be a dry powder inhaler. The inhaler could be a pressurised metered dose inhaler (pMDI). The inhaler could be a wet nebuliser.

The inhaler could be a tidal inhaler.

Said processor could be configured to determine said measure of the user's lung function and/or lung health by determining, from the data, peak inspiratory flow (PIF). Said processor could be configured to determine said measure of the user's lung function and/or lung health by determining, from the data, total inhaled volume.

The inhalation monitoring system could further comprise a user interface. Such a user interface could be configured to provide an indication of said measure of the user's lung function and/or lung health to the user. Such a user interface could be configured to provide an indication of said measure of the user's lung function and/or lung health to a caregiver. Such a user interface could be configured to provide an indication of said measure of the user's lung function and/or lung health to a medical professional.

Said indication could comprise an absolute value. Said indication could comprise a relative value. Said indication could comprise a binary health indicator. Said indication could comprise a tertiary indicator of whether the measure is above, below, or within a safe zone.

Said indication could be dependent upon data relating to the user.

The inhalation monitoring system could further comprise a transmitter. Said transmitter could be wireless.

Said transmitter could be configured to send the data to a user device for processing. Said transmitter could be configured to send the data to a user device for storage.

Said transmitter could be configured to send the data to a user device for provision to the user. Said transmitter could be configured to send the data to a user device for provision to a caregiver. Said transmitter could be configured to send the data to a user device for provision to a medical professional.

Said transmitter could be configured to send the data to a server for processing. Said transmitter could be configured to send the data to a server for storage. Said transmitter could be configured to send the data to a server for provision to the user. Said transmitter could be configured to send the data to a server for provision to a caregiver. Said transmitter could be configured to send the data to a server for provision to a medical professional.

Said transmitter could be configured to send the data to a data cloud for storage.

Said transmitter could be configured to send said measure to a user device for processing. Said transmitter could be configured to send said measure to a user device for storage. Said transmitter could be configured to send said measure to a user device for provision to the user. Said transmitter could be configured to send said measure to a user device for provision to a caregiver. Said transmitter could be configured to send said measure to a user device for provision to a medical professional.

Said transmitter could be configured to send said measure to a server for processing. Said transmitter could be configured to send said measure to a server for storage. Said transmitter could be configured to send said measure to a server for provision to the user. Said transmitter could be configured to send said measure to a server for provision to a caregiver. Said transmitter could be configured to send said measure to a server for provision to a medical professional.

Said transmitter could be configured to send said measure to a data cloud for storage.

U.S. Provisional Patent App. Nos. 62/011,808 and 62/135,798, which are each incorporated by reference herein in their entirety, describe an interface device that supports communications between a medical device and an electronic device. Such an interface could be utilized in the inhalation monitoring system that is described herein.

Said processor could be comprised in said inhaler. Said inhalation monitoring apparatus could be comprised in said inhaler. Said inhalation monitoring apparatus could be configured to be connected to said inhaler such that it is in pneumatic communication with a flow channel thereof. Said user interface could be comprised in said inhaler. Said transmitter could be comprised in said inhaler.

Said inhalation monitoring apparatus could comprise a pressure sensor. said pressure sensor could be a microelectromechanical system (MEMS) pressure sensor. Said pressure sensor could be a barometric MEMS pressure sensor. Said pressure sensor could be a nanoelectromechanical system (NEMS) pressure sensor.

Said inhalation monitoring apparatus could be configured to gather the data by sampling a pressure differential or absolute pressure at a series of time points.

Said sampling could be periodic. Said sampling period could be approximately 50 ms. The sampling frequency could be 100 Hz, for example.

Said medicament delivery apparatus could be further configured to deliver medicament to the user during a further inhalation of the user subsequent to said inhalation. The further inhalation may be a new breath by the user using a tidal inhaler, or a continuation of the first inhalation by the user using a dry-powder inhaler, for example. Said inhalation monitoring apparatus could be further configured to, during said further inhalation, gather further data for determining a further measure of the user's lung function and/or lung health. Said processor could be further configured to receive said further data from the inhalation monitoring apparatus. Said processor could be further configured to, using the further data, determine a further measure of the user's lung function and/or lung health. Said processor could be further configured to make a comparison of the data with the further data. Said processor could be further configured to make a comparison of the measure of the user's lung function and/or lung health with said further measure of the user's lung function and/or lung health.

The processor could be further configured to determine efficacy of usage of said inhaler using said comparison.

The processor could be further configured to predict future changes to the user's lung function and/or lung health using said comparison.

Said future changes to the user's lung function and/or lung health could comprise exacerbations of an existing respiratory condition such as asthma or chronic obstructive pulmonary disease (COPD).

The inhalation monitoring system could be configured to provide an alert to the user in response to said processor predicting one of a predetermined set of future changes to the user's lung function and/or lung health. The inhalation monitoring system could be configured to provide an alert to a caregiver in response to said processor predicting one of a predetermined set of future changes to the user's lung function and/or lung health. The inhalation monitoring system could be configured to provide an alert to a medical professional in response to said processor predicting one of a predetermined set of future changes to the user's lung function and/or lung health.

Said prediction could use data collected from subjects other than the user.

Said processor could be configured to determine said measure of the user's lung function and/or lung health using a mathematical model such as a regression model.

Said mathematical model could be of the correlation between total inhaled volume and forced expiratory volume in 1 second (FEU. Said mathematical model could be of the correlation between peak inspiratory flow (PIF) and forced expiratory volume in 1 second ($FEV_1$). Said mathematical model could be of the correlation between total inhaled volume and peak expiratory flow (PEF). Said mathematical model could be of the correlation between peak inspiratory flow (PIF) and peak expiratory flow (PEF).

For a multiple inhalation tidal inhaler or nebulizer, said mathematical model could be of the correlation between forced expiratory volume in 1 second ($FEV_1$) and the rate of change of the expiratory flow.

For a single inhalation dry-powder inhaler, a measurement of the user's lung function and/or lung health may be based upon a single breath by a user. For a tidal inhaler or nebulizer, the measurement may be based upon multiple breaths by the user. It is envisioned that outlying data points generated by the multiple breaths may be rejected, leaving only the good data points available for data processing.

The mathematical model could take into account biometric data for the user.

Said biometric data could comprise gender. Said biometric data could comprise age. Said biometric data could comprise height. Said biometric data could comprise weight.

The inhalation monitoring system could further comprise a user interface device operable to switch on and/or off said medicament delivery apparatus such that, when the medicament delivery apparatus is switched off, said inhaler is usable as a spirometer.

Said user interface device could comprise a mouthpiece cover of the inhaler. Said mouthpiece cover could be coupled to the medicament delivery apparatus such that a dose of medicament is made available for inhalation through a mouthpiece of the inhaler each time said cover is opened. The medicament delivery apparatus could be configured such that no further doses of medicament can be made available for inhalation through said mouthpiece until the cover has been completely closed and opened again.

The inhalation monitoring system could further comprise a placebo inhaler device. Said placebo inhaler device could comprise said inhalation monitoring apparatus. Said placebo inhaler device could be configured to be operably connected to said inhalation monitoring apparatus. Said placebo inhaler device could present substantially the same inhalation flow resistance to a user as said inhaler.

The inhalation monitoring system could comprise a battery configured to power the medicament delivery apparatus. The inhalation monitoring system could comprise a battery configured to power the inhalation monitoring apparatus. The inhalation monitoring system could comprise a battery configured to power the processor.

The inhalation monitoring system could further comprise memory configured to store the data. The inhalation monitoring system could further comprise memory configured to store said measure.

According to a second aspect there is provided a method comprising: using an inhaler, delivering medicament to a user during an inhalation of the user; during said inhalation, gathering data for determining a measure of the user's lung function and/or lung health; and using the data, making a determination of a measure of the user's lung function and/or lung health.

The inhaler could be a dry powder inhaler. The inhaler could be a pressurised metered dose inhaler (pMDI). The inhaler could be a wet nebuliser. The inhaler could be a tidal inhaler.

Said determination could be made by determining, from the data, peak inspiratory flow (PIF). Said determination could be made by determining, from the data, total inhaled volume.

The method could further comprise providing an indication of said measure of the user's lung function and/or lung health to the user by means of a user interface. The method could further comprise providing an indication of said measure of the user's lung function and/or lung health to a caregiver by means of a user interface. The method could further comprise providing an indication of said measure of the user's lung function and/or lung health to a medical professional by means of a user interface.

Said indication could comprise an absolute value. Said indication could comprise a relative value. Said indication could comprise a binary health indicator. Said indication could comprise a tertiary indicator of whether the measure is above, below, or within a safe zone.

Said indication could be dependent upon data relating to the user.

The method could further comprise, by means of a transmitter, sending the data to a user device for processing. The method could further comprise, by means of a transmitter, sending the data to a user device for storage. The method could further comprise, by means of a transmitter, sending the data to a user device for provision to the user. The method could further comprise, by means of a transmitter, sending the data to a user device for provision to a caregiver. The method could further comprise, by means of a transmitter, sending the data to a user device for provision to a medical professional.

The method could further comprise, by means of a transmitter, sending the data to a server for processing. The method could further comprise, by means of a transmitter, sending the data to a server for storage. The method could further comprise, by means of a transmitter, sending the data to a server for provision to the user. The method could further comprise, by means of a transmitter, sending the data to a server for provision to a caregiver. The method could further comprise, by means of a transmitter, sending the data to a server for provision to a medical professional.

The method could further comprise, by means of a transmitter, sending the data to a data cloud for storage.

The method could further comprise, by means of a transmitter, sending said measure to a user device for processing. The method could further comprise, by means of a transmitter, sending said measure to a user device for storage. The method could further comprise, by means of a transmitter, sending said measure to a user device for provision to the user. The method could further comprise, by means of a transmitter, sending said measure to a user device for provision to a caregiver. The method could further comprise, by means of a transmitter, sending said measure to a user device for provision to a medical professional.

The method could further comprise, by means of a transmitter, sending said measure to a server for processing. The method could further comprise, by means of a transmitter, sending said measure to a server for storage. The method could further comprise, by means of a transmitter, sending said measure to a server for provision to the user. The method could further comprise, by means of a transmitter, sending said measure to a server for provision to a caregiver. The method could further comprise, by means of a transmitter, sending said measure to a server for provision to a medical professional.

The method could further comprise, by means of a transmitter, sending said measure to a data cloud for storage.

Said transmitter could be a wireless transmitter.

As noted above, according to the second aspect of the invention, there is provided a method comprising: using an inhaler, delivering medicament to a user during an inhalation of the user; during said inhalation, gathering data for determining a measure of the user's lung function and/or lung health; and using the data, making a determination of a measure of the user's lung function and/or lung health.

Said gathering could be done by said inhaler. Said determination could be made by said inhaler.

Said gathering could be done by inhalation monitoring apparatus. Said method could further comprise connecting said inhalation monitoring apparatus to the inhaler such that the inhalation monitoring apparatus is in pneumatic communication with a flow channel of the inhaler.

Said user interface could be comprised in said inhaler. Said transmitter could be comprised in said inhaler.

Said gathering could be performed by means of a pressure sensor. Said pressure sensor could be a microelectromechanical system (MEMS) pressure sensor. Said pressure sensor could be a barometric MEMS pressure sensor. Said pressure sensor could be a nanoelectromechanical system (NEMS) pressure sensor.

Said data gathering could comprise sampling a pressure differential at a series of time points. Said data gathering could also comprise sampling an absolute pressure at a series of time points.

Said sampling could be periodic.

Said sampling period could be approximately 50 ms. The sampling frequency could be 100 Hz, for example.

The method could further comprise delivering medicament to the user during a further inhalation of the user subsequent to said inhalation. The method could further comprise during said further inhalation, gathering further data for determining a further measure of the user's lung function and/or lung health. The method could further comprise using the further data, making a determination of a further measure of the user's lung function and/or lung health. The method could further comprise making a comparison of the data with the further data. The method could further comprise making a comparison of the measure of the user's lung function and/or lung health with said further measure of the user's lung function and/or lung health.

The method could further comprise determining efficacy of usage of said inhaler using said comparison.

The method could further comprise predicting future changes to the user's lung function and/or lung health using said comparison.

Said future changes to the user's lung function and/or lung health could comprise exacerbations of an existing respiratory condition such as asthma, chronic obstructive pulmonary disease (COPD), respiratory syncytial virus (RSV), Cystic Fibrosis (CF), diopathic pulmonary fibrosis (IPF), or pulmonary embolism (PE).

The method could further comprise providing an alert to the user in response to said predicting. The method could further comprise providing an alert to a caregiver in response to said predicting. The method could further comprise providing an alert to a medical professional in response to said predicting.

Said prediction could use data collected from subjects other than the user.

Said determination of said measure of the user's lung function and/or lung health could use a mathematical model. Said mathematical model could be a regression model.

Said mathematical model could be of the correlation between total inhaled volume and forced expiratory volume in 1 second (FEU. Said mathematical model could be of the correlation between peak inspiratory flow (PIF) and forced expiratory volume in 1 second ($FEV_1$) Said mathematical model could be of the correlation between total inhaled volume and peak expiratory flow (PEF). Said mathematical model could be of the correlation between peak inspiratory flow (PIF) and peak expiratory flow (PEF).

The mathematical model could take into account biometric data for the user.

Said biometric data could comprise gender. Said biometric data could comprise age. Said biometric data could comprise height. Said biometric data could comprise weight.

The method could further comprise: switching off a medicament delivery function of the inhaler; and using the inhaler as a spirometer.

For a single inhalation dry-powder inhaler, for example, switching off said medicament delivery function could comprise opening a mouthpiece cover of the inhaler. Said cover could be configured such that a dose of medicament is made available for inhalation through a mouthpiece of the inhaler each time the cover is opened. The inhaler could be configured such that no further doses of medicament can be made available for inhalation through the mouthpiece until the cover has been completely closed and opened again.

The method could further comprise using a placebo inhaler device.

Said gathering could be performed by inhalation monitoring apparatus. Said placebo inhaler device could comprise said inhalation monitoring apparatus. Said placebo inhaler device could be configured to be operably connected to said inhalation monitoring apparatus.

Said placebo inhaler device could present substantially the same inhalation flow resistance to a user as said inhaler. For a multiple inhalation tidal inhaler or a wet nebulizer, which may have a lower inhalation flow resistance than a dry-powder inhaler, it may be advantageous to use a special non-drug cartridge having a defined inhalation flow resistance. The non-drug cartridge could electronically identify itself to the inhaler by the same means that is used to identify the drug within a cartridge, e.g., via an electrically erasable programmable read-only memory.

The method could further comprise storing the data and/or said measure in memory.

BRIEF DESCRIPTION OF THE DRAWING FIGURES

Aspects of the present invention will now be described by way of example with reference to the accompanying figures. In the figures.

Figure 2:
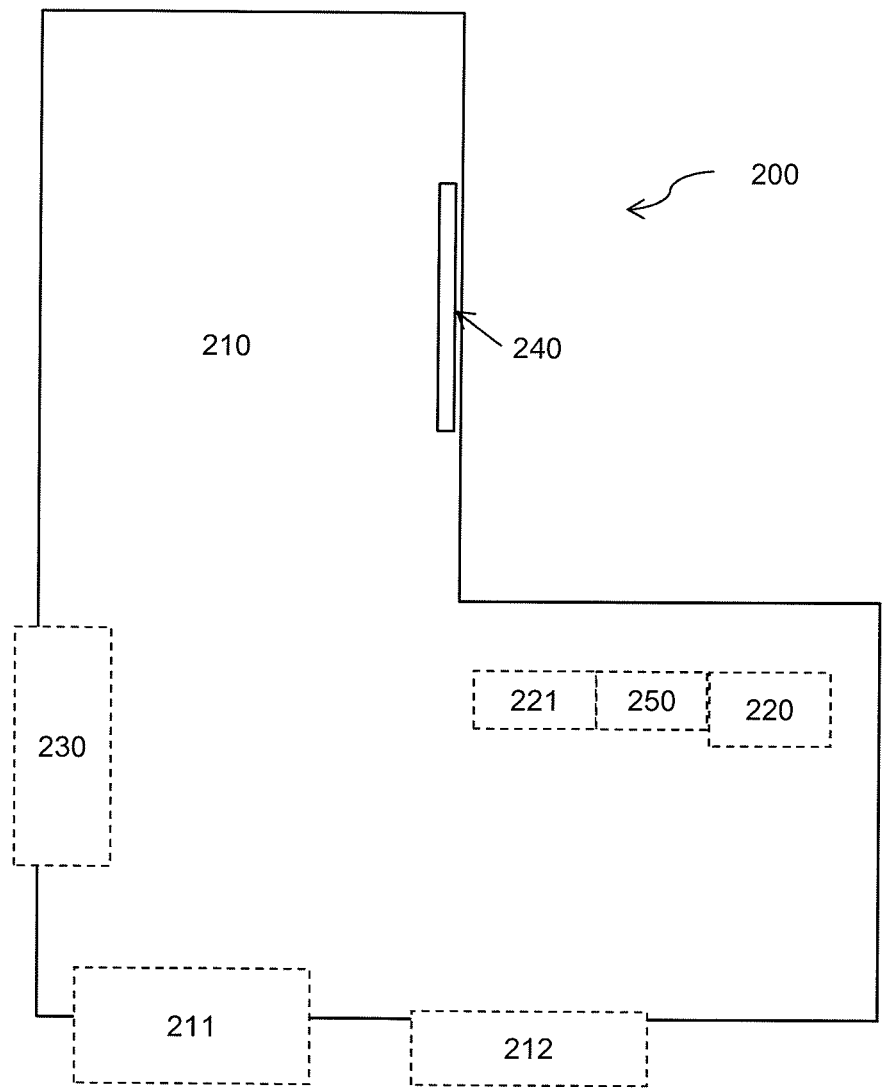

FIG. 2 schematically illustrates an example inhalation monitoring system; and

Figure 3:
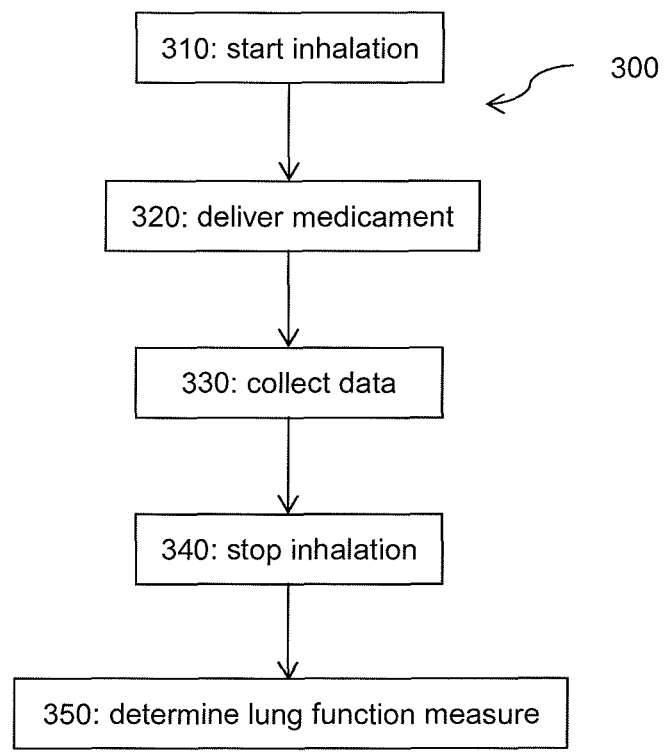

FIG. 3 is a flowchart of an example inhalation monitoring method.

DETAILED DESCRIPTION OF THE INVENTION

The following description is presented to enable any person skilled in the art to make and use the system, and is provided in the context of a particular application. Various modifications to the disclosed embodiments will be readily apparent to those skilled in the art.

The general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

Many lung patients are prescribed inhalers so that they or a caregiver can administer medicament to them as a routine preventative measure, to ease an exacerbation, or both. Such patients and caregivers are trained in the use of these inhalers and become very familiar with them. It is therefore proposed to monitor patients' lung function using their inhalers. Monitoring lung health while administering medication reduces the time and effort required from patients, caregivers and medical professionals to manage lung conditions.

This has not been previously considered since, as explained above, lung function is generally assessed using expiratory measures and dry powder inhalers, for example, are not generally designed to permit exhalation. In some cases, for example some dry powder inhalers, exhalation into inhalers can impair their function (e.g. if moisture from an exhalation causes powdered medicament to form clumps, making even administration more difficult).

Figure 1A:
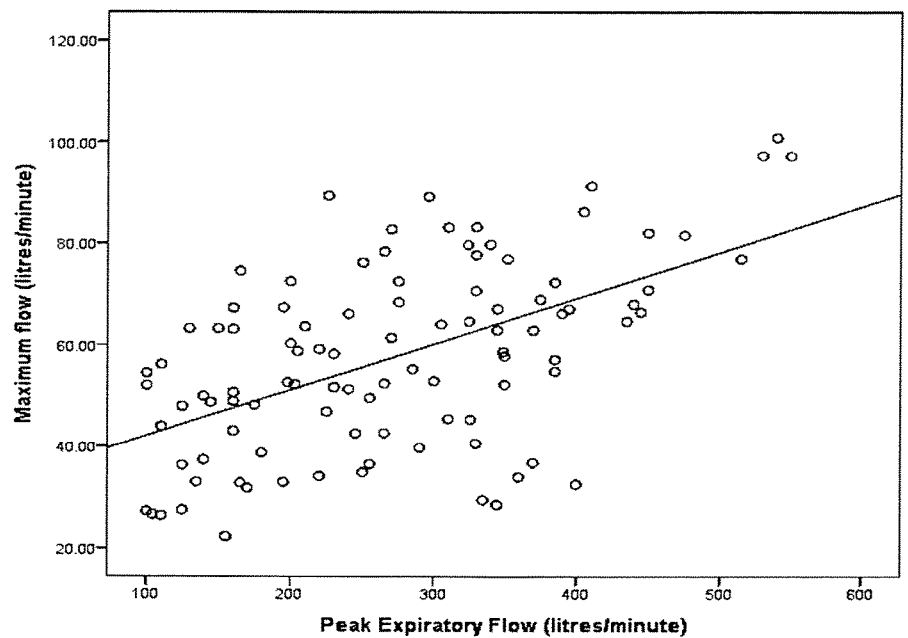
FIG. 1a illustrates a correlation between PEF and the maximum flow measured during inhalation.
Figure 1B:
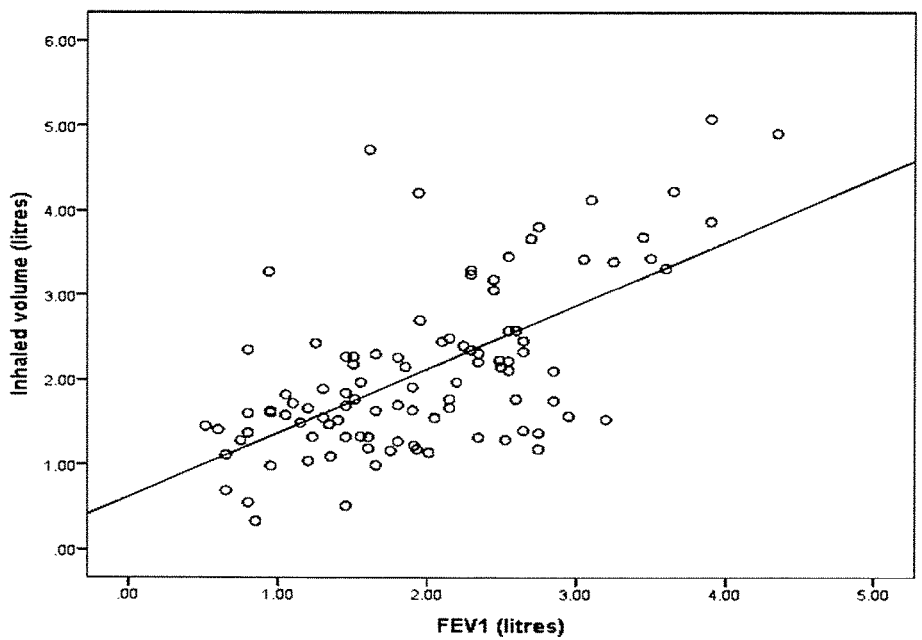
FIG. 1b illustrates a correlation between $FEV_1$ and total inhaled volume.

However, the applicant has established that there are correlations between some expiratory measures of lung function and some inspiratory measures. For example, see FIG. 1a, showing a correlation between PEF and the maximum flow measured during inhalation (peak inspiratory flow, PIF), and FIG. 1b, showing a correlation between $FEV_1$ and total inhaled volume. Regression lines and their equations are indicated on the plots, where:

$x_1$=gender (male=0; female=1)
$x_2$=age/years
$x_3$=height/cm
$x_4$=weight/kg
$x_5$=PEF/l·min$^{-1}$
$x_6$=FEV1/l·min$^{-1}$ $y_1$=inhaled volume/I
$y_2$=PIF/I It is therefore proposed to process inhalation data gathered while administering medicament with an inhaler in order to determine lung function and/or health.

FIG. 2 schematically illustrates an example inhalation monitoring system 200. An inhaler 210 comprises medicament delivery apparatus 211. This could for example be as per the dry powder inhalers described in any of PCT patent application publication numbers WO 01/97889, WO 02/00281, WO 2005/034833 or WO 2011/054527, which are incorporated in their entirety herein. Inhalation monitoring systems could also comprise other types of inhalers/nebulisers, e.g. pressurised metered dose inhalers (pMDIs) or wet nebulisers. The inhalers could require forced inspiratory manoeuvres or only tidal breathing.

Inhalation monitoring apparatus 220 may also be comprised in the inhaler as shown, or may be comprised in a separate unit connected to it. The inhalation monitoring apparatus could for example comprise a miniature (e.g. microelectromechanical, MEMS, or nanoelectromechanical, NEMS) pressure sensor as described in any of U.S. patent application Nos. 62/043,126 to Morrison, 62/043,120 to Morrison, and 62/043,114 to Morrison, which are incorporated in their entirety herein. Other suitable arrangements could be envisaged. For those making use of a pressure sensor, said sensor should be in pneumatic communication with an airflow channel of the inhaler through which the user inhales.

A processor 230 communicates with the inhalation monitoring apparatus in order to process data collected by the inhalation monitoring apparatus to determine a measure of the user's lung function and/or health. The processor could be comprised in the inhaler as shown, or if the inhalation monitoring apparatus is comprised in a separate accessory unit, the processor could also be comprised in said accessory unit. Alternatively, if the inhalation monitoring apparatus is equipped with a wired or wireless transmitter 221, the processor could be in a separate device, for example a user device such as a smartphone, tablet, laptop or PC. If the inhalation monitoring apparatus is equipped with a transmitter capable of communicating with a network such as the internet, the processing could be done remotely, for example at a medical professional's PC or on a health service, inhaler manufacturer or cloud server. (Any of the abovementioned devices or servers could also be used for data storage.) Optionally, processor 230 could be made up of multiple processors in any of the abovementioned locations, for example some basic processing may be done on board the inhaler, while more detailed analysis is offloaded to a remote device or server.

The inhaler could optionally comprise a user interface 240 for providing information relating to use of the inhaler and/or determined lung function and/or lung health. This could, for example, be a screen, indicator light, indicator buzzer, speaker, traditional dose counter tape, vibrating alert etc. or any combination of these or similar. Alternatively, such information could be provided via one or more user interfaces of a user device of the patient or a caregiver or medical professional.

The system could also comprise a memory 250 for storing the collected data, calculation results and computer code instructions for execution by the processor. As with the processor, the memory could be located in the inhaler or an external device or server.

The electronic component of the inhaler could be powered by a battery 212 so that the inhaler can be portable.

The inhaler could further comprise switching means for putting the medicament delivery apparatus in or out of operation. When the medicament delivery apparatus is not functioning, the inhaler can be used as a spirometer. As one example, electronic switching means could be provided if the medicament delivery apparatus is under electronic (e.g. push-button) control. As another example, PCT patent application publication number WO 2005/034833, which is incorporated by reference herein in its entirety, describes a mechanism for a metered dose dry powder inhaler in which a metering cup measures out a dose of medicament from a hopper and is moved to a dosing position by action of a yoke linked to a mouthpiece cover. Thus, opening the mouthpiece cover primes the inhaler for use and once a dose has been inhaled, further dosing is not possible until the cover has been closed and opened again. Using such an inhaler with the inhalation monitoring apparatus proposed herein, a patient could take their dose of medicament and, before closing the mouthpiece cover, make one or more further inhalations through the mouthpiece for the purposes of further data collection. This allows greater volumes of data to be collected without risking the patient over-dosing. As yet another example, a spirometer cartridge could be connected to a replaceable cartridge tidal inhaler, and a patient could make one or more further inhalations through the spirometer cartridge for the purpose of further data collection.

Alternatively, the inhaler described above could be provided in a kit with a placebo or dummy inhaler which has a similar flow resistance to the real inhaler, but which either does not comprise medicament delivery apparatus, is empty or is loaded with a placebo substance such as lactose. The placebo inhaler could comprise similar inhalation monitoring apparatus to that described above, or could be connectable to such apparatus.

If inhaler 210 were a wet nebulizer, for example, then all of the electronic components could be located in a module that is removably connected to the inhalation port in order to protect the electronics from exposure to fluid. The module could be configured to be connected to different wet nebulizers of varying shape and size. The module could include a flow channel having a defined inhalation flow resistance that is higher than the inhalation flow resistance of the wet nebulizer alone (i.e., without the module).

FIG. 3 is a flowchart of an example inhalation monitoring method 300. At 310, inhalation (through an inhaler) commences. At 320, medicament is delivered via the inhaler. At 330, data concerning said inhalation is collected. At 340, inhalation ends. At 350, the data is processed to make a determination of a measure of lung function and/or lung health. The order of steps 320 and 330 could be reversed or they could be carried out partially or fully in parallel. Step 350 could occur before, during or after 340 and before, after, or fully or partially in parallel with 320.

The data could also be used for adherence monitoring by a medical practitioner, i.e., to ensure that the inhaler is being used properly by the user.

The processing could comprise use of a mathematical model such as the regression models illustrated in FIG. 1.

Method 300 could be repeated each time the inhaler is used, which could for example be daily. Data gathered from multiple uses of the inhaler and/or determinations made from the data could be stored and compared to provide an indication of the progression of a condition over time. This information could be used to determine efficacy of the current treatment regime and inform any changes which may be required. The processor may also be capable of using the data and/or determinations to predict future changes in lung function and/or lung health. This prediction could be based only on data collected from the patient in question, or could incorporate data collected from other patients too. For example, data from users of many inhalers as described above could be collated and used to identify patterns in inhalation data changes preceding exacerbations of particular lung conditions. The processing logic could thus be self-learning. If a particular patient's data is then seen to match the beginning of such a pattern, they or their caregiver or medical practitioner could be alerted so that any required changes to a treatment regime (for example increased dosage, additional medications or therapies) can be made to help avoid an exacerbation.

The data collected by the inhalation monitoring apparatus could be, for example, a time series of pressure differential measurements or absolute pressure measurements. Measurements could be made periodically, for example every 10 ms, 50 ms or 100 ms over e.g. 2, 5 or 10 seconds. Data collection may be reset between uses of the inhalation monitoring apparatus.

The user interface could provide a numerical value, for example of measured PIF, calculated total inhaled volume, calculated PEF, calculated FEV1 or a fraction or percentage of one of these relative to an ideal value for the particular patient (said ideal value could be chosen based on biometric data such as age, gender, height, weight etc.). Alternatively it could provide a binary indicator as to whether or not the measured value is within a healthy range, or a tertiary indicator as to whether the measured value is below, above or within a healthy range. Boundaries of such a healthy range could again depend on biometric data stored for the particular patient. The user interface could alternatively or additionally be used to indicate number of doses taken or number of doses remaining in a disposable inhaler, refillable hopper or disposable cartridge. Another alternative or additional indication could be whether the inhaler has been used correctly, for example so that the patient or a caregiver or medical professional is alerted to missed doses, inhalations that are too short or weak for effective drug administration, or that medication has otherwise been taken incorrectly, and/or receives confirmation that medication has been taken correctly.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

What is claimed is:

1. A method of inhalation monitoring, the method comprising:
    delivering a dose of medicament to a user as a result of the user inhaling via an airflow channel of an inhaler;
    providing a pressure measurement via a pressure sensor that is in pneumatic communication with the airflow channel of the inhaler, wherein the pressure measurement is provided based on the user inhaling via the airflow channel of the inhaler;
    determining an inspiratory measure based on the pressure measurement; and
    determining an expiratory measure based on the inspiratory measure, wherein the expiratory measure is indicative of a lung function of the user.

2. The method of claim 1, further comprising:
    making the dose of the medicament available for inhalation when a mouthpiece cover of the inhaler is opened.

3. The method of claim 1, wherein the inspiratory measure comprises a total inhaled volume and the expiratory measure comprises a forced expiratory volume in 1 second ($FEV_1$).

4. The method of claim 1, wherein the inspiratory measure comprises a peak inspiratory flow (PIF) and the expiratory measure comprises a forced expiratory volume in 1 second ($FEV_1$).

5. The method of claim 1, wherein the inspiratory measure comprises a total inhaled volume and the expiratory measure comprises a peak expiratory flow (PEF).

6. The method of claim 1, wherein the inspiratory measure comprises a peak inspiratory flow (PIF) and the expiratory measure comprises a peak expiratory flow (PEF).

7. The method of claim 1, wherein the pressure measurement is associated with multiple inhalations by the user.

8. The method of claim 1, wherein the expiratory measure is determined based on biometric data of the user, the biometric data of the user comprising at least one of gender, age, height, or weight.

9. The method of claim 1, further comprising:
    sending, via a transmitter, the expiratory measure indicative of the lung function of the user.

10. A system for inhalation monitoring, the system comprising:
    a medicament delivery apparatus comprising a mouthpiece, an airflow channel, and medicament, wherein the medicament delivery apparatus is configured to deliver a dose of the medicament to a user as a result of the user inhaling via the airflow channel of the medicament delivery apparatus;
    a monitoring apparatus comprising a pressure sensor, wherein the pressure sensor is in pneumatic communication with the airflow channel and wherein the pressure sensor is configured to provide at least one pressure measurement based on the user's inhalation via the mouthpiece to receive a dose of the medicament via the airflow channel; and
    a processor configured to:
        receive the at least one pressure measurement;
        determine an inspiratory measure based on the at least one pressure measurement; and
        determine an expiratory measure based on the inspiratory measure, wherein the expiratory measure is indicative of a lung function of the user.

11. The system of claim 10, wherein the medication delivery apparatus further comprises a mouthpiece cover, and
    wherein the medication delivery apparatus is configured to make the dose of the medicament available for inhalation when the mouthpiece cover is opened.

12. The system of claim 10, wherein the inspiratory measure comprises a total inhaled volume and the expiratory measure comprises a forced expiratory volume in 1 second ($FEV_1$).

13. The system of claim 10, wherein the inspiratory measure comprises a peak inspiratory flow (PIF) and the expiratory measure comprises a forced expiratory volume in 1 second ($FEV_1$).

14. The system of claim 10, wherein the inspiratory measure comprises a total inhaled volume and the expiratory measure comprises a peak expiratory flow (PEF).

15. The system of claim 10, wherein the inspiratory measure comprises a peak inspiratory flow (PIF) and the expiratory measure comprises a peak expiratory flow (PEF).

16. The system of claim 10, wherein the at least one pressure measurement is associated with multiple inhalations by the user.

17. The system of claim 10, wherein the expiratory measure is determined based on biometric data of the user, the biometric data of the user comprising at least one of gender, age, height, or weight.

18. The system of claim 10, wherein the processor is part of a user device.

19. The system of claim 10, wherein the processor is part of a server.

20. The system of claim 10, wherein the processor is part of the monitoring apparatus.

21. The system of claim 10, wherein the system further comprises:
a transmitter configured to send the expiratory measure indicative of the lung function of the user.

22. A medicament delivery apparatus, the medicament delivery apparatus comprising:
a mouthpiece;
an airflow channel;
medicament, wherein the medicament delivery apparatus is configured to deliver a dose of the medicament to a user as a result of the user inhaling via the airflow channel of the medicament delivery apparatus;
a pressure sensor, wherein the pressure sensor is in pneumatic communication with the airflow channel and wherein the pressure sensor is configured to provide at least one pressure measurement when a user inhales via the mouthpiece to receive a dose of the medicament via the airflow channel; and
a processor configured to:
receive the at least one pressure measurement;
determine an inspiratory measure based on the at least one pressure measurement; and
determine an expiratory measure based on the inspiratory measure, wherein the expiratory measure is indicative of a lung function of the user.

23. The medicament delivery apparatus of claim 22, wherein the inspiratory measure comprises at least one of a peak inspiratory flow (PIF) or a total inhaled volume, and the expiratory measure comprises at least one of a forced expiratory volume in 1 second ($FEV_1$) or a peak expiratory flow (PEF).

24. The medicament delivery apparatus of claim 22, wherein the inspiratory measure comprises a peak inspiratory flow (PIF) and the expiratory measure comprises a peak expiratory flow (PEF).

* * * * *